United States Patent [19]
Bruno et al.

[11] Patent Number: 6,084,683
[45] Date of Patent: Jul. 4, 2000

[54] OPTICAL DETECTION APPARATUS FOR CHEMICAL ANALYSES OF SMALL VOLUMES OF SAMPLES

[76] Inventors: Alfredo Emilio Bruno, Auf der Wacht 10B, 4104 Oberwil, Switzerland; Steven Mark Barnard, 5220 Flore Terrace Apt. M304, San Diego, Calif. 92122; Markus Ehrat, Im Brüel 6, 4312 Magden, Switzerland; Reinhard Völkel, rue Matile 8, 2000 Neuchâtel, Switzerland; Philippe Nussbaum, rue Jolimont 4, 2000 Neuchâtel, Switzerland; Hans Peter Herzig, Bel-Air 11, 2000 Neuchâtel, Switzerland

[21] Appl. No.: 09/194,523
[22] PCT Filed: May 27, 1997
[86] PCT No.: PCT/EP97/02745
  § 371 Date: Nov. 25, 1998
  § 102(e) Date: Nov. 25, 1998
[87] PCT Pub. No.: WO97/45718
  PCT Pub. Date: Dec. 4, 1997

[30] Foreign Application Priority Data

May 28, 1996 [EP] European Pat. Off. ............... 9681034

[51] Int. Cl.⁷ .................................................. G01N 21/03
[52] U.S. Cl. .......................... 356/446; 356/440; 356/246; 422/82.09
[58] Field of Search ..................... 356/446, 244, 356/246, 440; 435/808; 422/82.05, 82.08, 82.09

[56] References Cited

U.S. PATENT DOCUMENTS

| | | |
|---|---|---|
| 4,254,084 | 3/1981 | Blum ........................................ 422/81 |
| 5,039,490 | 8/1991 | Marsoner et al. .................... 422/82.01 |

FOREIGN PATENT DOCUMENTS

| | | |
|---|---|---|
| 0 571 661 A1 | 12/1993 | European Pat. Off. . |
| 44 29 846 A1 | 3/1995 | Germany . |

OTHER PUBLICATIONS

Czolk, R., "Bewaehrungsprobe fuer Mikrosysteme", F&M Feinwerktechnik & Messtechnik 103, Sep., No. 9, 1995, pp. 492–494.

*Primary Examiner*—Richard A. Rosenberger
*Attorney, Agent, or Firm*—Wenderoth, Lind & Ponack, L.L.P.

[57] ABSTRACT

Optical detection apparatus for chemical analyses of small volumes of samples has light sources (21) to emit induction light, a measuring cell (7) for the sample, photoelectric sensing elements (22) to receive light coming form the sample in the measuring cell (7), as well as beam-conducting means for the induction light or the light from the sample. In the apparatus, several essentially planar, laminar components (2–7) are arranged in a sandwich structure, whereby the components (2–7) contain the light sources (21), the measuring cell (7), the photoelectric sensing elements (22), and also the beam conducting means.

29 Claims, 7 Drawing Sheets

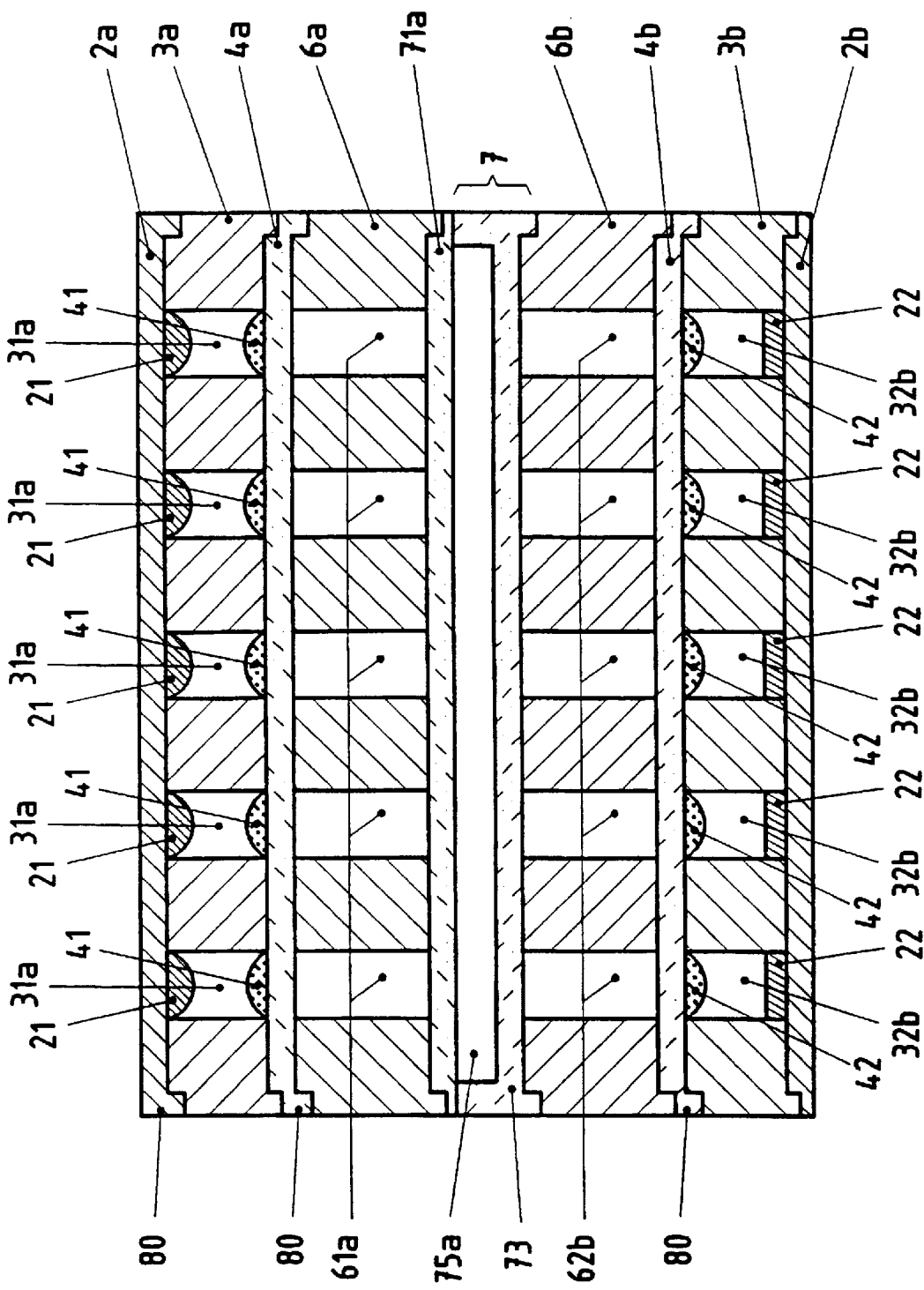

OPTICAL DETECTION APPARATUS FOR CHEMICAL ANALYSES OF SMALL VOLUMES OF SAMPLES

BACKGROUND OF THE INVENTION

The invention relates to an optical detection apparatus for chemical analyses of small volumes of samples.

Measuring apparatuses for the qualitative and quantitative chemical analyses of samples are known to the specialist in large number. For the analysis in particular of small volumes of samples, techniques are used today which are based for example on electrophoresis or chromatography, or in which the sample is examined optically without prior separation. In both cases, detection of the analytes to be identified is very often effected by means of optical methods, so that the development of new optical detection apparatus plays a very important role in respect of the instrumental improvement in the field of analysis. Even within the bounds of so-called immuno-assay, detection of biologically active substances is frequently effected by means of optical methods. Optical detection apparatuses include inter alia systems for absorption and fluorescence measurements.

In general, depending on type, detection apparatuses comprise a source of light to emit an induction light, a measuring cell for the sample, a photoelectric sensing element to receive the light coming from the sample in the measuring cell, and light-conducting means, on the one hand in order to conduct the induction light from the light source to the measuring cell, and on the other hand to conduct the light coming from the sample in the measuring cell back to the photoelectric sensing element.

In the case of fluorescence measurements, a known process is for example to bring the sample into contact with a sensor layer, e.g. a membrane applied to a substrate, the membrane containing chemical or biochemical recognition elements. As (bio-) chemical recognition elements, affinity partners of the analyte to be identified are immobilised in or on the membrane, and bind the analytes to them, for example by means of an antigen-antibody reaction. The sensor layer, which has selective sensitivity for the analyte to be identified in the sample, for example through the recognition elements, is brought to fluorescence by the induction light. When the sample makes contact with the sensor layer, the interaction between the analyte and the sensor layer or the recognition elements causes a change in the fluorescence light, for example in respect of its intensity, which is recorded by the photoelectric sensing element and is registered as the measured variable.

Frequently in the development of new detection apparatus, the main aim is to be able to carry out the analyses faster and faster and to miniaturize the apparatus more and more, so that the amount of sample employed is as small as possible. At the same time, however, the instrumental sensitivity of measurement should at the very least be maintained. In addition, it is frequently necessary to examine a sample qualitatively and quantitatively as quickly as possible for various analytes. For example, the routine examination of blood in hospitals and laboratories requires that the sample, namely blood, is examined in respect of different analytes, e.g. the partial pressure of so-called blood gases, such as carbon dioxide and oxygen, the concentration of electrolytes, such as $H^+$ (pH value), $Na^+$, $K^+$, $Ca^{2+}$, $Cl^-$, or for its metabolite content, such as lactate, glucose or creatinine. In agro-technology also, it is often necessary to example a sample in respect of several analytes.

An optical detection apparatus, which is equipped for the examination of small volumes of samples, is disclosed in EP-A-0 616 211. The fundamental idea here is to keep to a minimum the number of optical transitions—by which is meant the transitions in the optical path between areas of differing optical density—between the source of light and the photoelectric sensing element. This is achieved, whereby the induction light emitted from the light source is conducted by a special photoconductor, which has a refractive index gradient, for example a gradient index (GRIN) lens, to a capillary tube containing the substance, and the light coming from the sample in the capillary tube is conducted by a further photoconductor to the photoelectric sensing element. In all the transition areas between the individual optical elements, there is an index adaptation medium, the refractive index of which conforms basically with that of the wall material of the capillary tube. In addition, this index adaptation medium provides a mechanically stable link of the individual optical elements. This concept, called "pigtailing", has the advantage that the induction light and the light from the sample, with the exception of the interior of the capillary tube, always travel in the media at an essentially constant optical density. Thus, disadvantageous scattered light effects are reduced. The mechanically stable set-up has the advantage that vibrations do not disturb the optical path of light.

Although such detection apparatuses have proved to be very advantageous, there are a few applications for which they are not optimally suited. For example, if the detection apparatus is to be designed for examination in respect of several analytes in one sample, in general several light sources would be needed, as well as several induction light conductors and several photoconductors for the sample, which respectively include GRIN lenses, optical light-wave conductors or similar optical elements, in order to effect several essentially separate light paths for the individual measurements. For optimum functioning, it is necessary that the distinct elements, such as light source, photoconductors, optical filters, photoelectric sensing elements, are adjusted extremely precisely relative to one another. Each of the elements must be individually very carefully positioned with respect to its adjacent elements, and subsequently fixed by joining with the index adaptation medium. Thus, the preparation of the optical section is already associated with a relatively high amount of work. In addition, the induction light conductor and the sample photoconductor must be of very exact dimensions and positioned and secured exactly on the capillary tube in order to attain illumination of the sample which is as efficient as possible, and in order to optimise the intensity of light from the sample contacting the photoelectric sensing element. Also, the GRIN lenses frequently used as photoconductors are relatively expensive compared with other optical elements, and some experience and time is needed to incorporate these in the optical light path with exact dimensioning and positioning. Normally, these operations must be carried out by hand. Even if such an expenditure of time and money is not of primary importance to applications for research purposes, for off-site applications outside of research laboratories in respect of efficient mass-production of these detection apparatuses, it is much more relevant. As the number of different analytes to be identified increases, the production outlay also increases, since for each of the individual light paths, the elements forming it have to be adjusted individually.

As the number of analytes to be measured increases, however, the size of the detection apparatus also increases, if only for the reason that more optical elements have to be present. Since for example GRIN lenses must have certain dimensions for physical reasons, the apparatus restricts the limits of miniaturization.

SUMMARY OF THE INVENTION

It is therefore an aim of the invention to produce an optical detection apparatus for chemical analyses of small volumes of samples, which in particular enables one sample to be examined in respect of several analytes. The apparatus should be very simple to assemble, without complicated positioning and adjustment work. Furthermore, it should be inexpensive and manufacturable by means of efficient mass-production, whilst allowing very good reproducibility. Moreover, the apparatus should be suitable for various types of optical measurements such as absorption measurements and fluorescence measurements. In addition, it should be possible to manufacture the apparatus in a compact form which is easy to handle, and it should be available for mobile usage in a wide field of applications even outside of modern research laboratories. Also, it should be possible to miniaturize the detection apparatus in a simple manner so as to comply with the growing demands for short analysis times and low consumption of samples. For example, using the apparatus, it should be possible to examine sample volumes in the range of a few $\mu l$ reliably and as exactly as possible in respect of the qualitative and quantitative presence of several analytes.

The optical detection apparatus for chemical analyses of small volumes of samples, which solves these problems, is characterized by the features of the present invention. In accordance with the invention, it is thus proposed that several essentially planar, laminar components are arranged in a sandwich structure, whereby these components contain the light sources, the measuring cell, the photoelectric sensing elements and the beam-conducting agents.

Since several sources of light and several photoelectric sensing elements are provided, the detection apparatus according to the invention includes several, essentially separate measuring units, so that the sample can be examined essentially simultaneously in respect of several analytes. The term "several separate measuring units" is understood to mean that there are several essentially optically separate light paths for measurement. These separate measuring units may be arranged e.g. in the form of a field (array).

Through the sandwich structure with several laminar components, the detection apparatus according to the invention may be made up very simply, namely by simply stacking the components on top of one another. Complicated adjustment and positioning work is not necessary here. This has the advantage that the different components may be individually exchanged as required, without having to carry out substantial manipulation of the other components.

It is preferable for at least the following components to be provided: one component containing several sources of light arranged on one plane; one component containing several photoelectric sensing elements arranged on one plane; one component containing several optical beam-conducting elements arranged on one plane; one component with the measuring cell for the sample; as well as at least one component containing channels to conduct light, especially in the form of ducts. By simply stacking these components on top of one another, an embodiment of the detection apparatus according to the invention is obtained, which contains the separate measuring units, and which respectively comprises one of the light sources, one of the photoelectric detectors, at least one of the optical elements, one light inlet channel formed by the light-conducting channels which admits the induction light to the measuring cell, as well as a light outlet channel, formed by the light-conducting channels, which conducts the light coming from the sample in the measuring cell to the photoelectric sensing element.

By providing these separate measuring units, the sample contained in the measuring cell may essentially be examined simultaneously in respect of several analytes.

What is particularly advantageous with this sandwich structure is the fact that all the separate measuring units can be adjusted in a single operation, namely when stacking the individual components on top of one another. It is no longer necessary to adjust each individual distinct element of a measuring unit in a specific operation.

The optical elements which serve to conduct the beam of induction light or light from the sample are preferably micro-optical elements, for example micro-lenses. It is advantageous if several of these optical elements are arranged for example in the form of a matrix on one plane. The reason for this is that such arrangements of micro-lenses can be produced inexpensively in a very simple manner by means of replication techniques which are known per se and in mass-production with very high reproducibility of their optical properties. In addition, the use of micro-optical elements is advantageous for the miniaturization of the detection apparatus according to the invention.

Through the sandwich structure with several individually exchangeable components, the detection apparatus according to the invention is very flexibly designed, and is suitable for a number of different areas of application. The detection apparatus according to the invention may be designed both for transmitted light measurements, for absorption measurements, and for incident light measurements, for example fluorescence measurements.

Further advantageous modes of action and variants of the detection apparatus according to the invention may be seen from the description.

BRIEF DESCRIPTION OF THE DRAWINGS

On the following pages, the invention will be clarified more fully using embodiments and drawings. In the schematic drawings, which are not to scale, are shown:

FIG. 7: a cross-section illustration of a second embodiment of the detection apparatus according to the invention.

DETAILED DESCRIPTION OF THE PREFERRED EMBODIMENTS

In the following description of the embodiments, using the drawings, identical parts or those having equivalent functions are given the same reference number. The optical detection apparatus according to the invention for chemical analyses of small volumes of samples typically comprises light sources 21 (FIG. 1) to emit induction light, a measuring cell 7 for the sample, photoelectric sensing elements 22 to receive light coming from the sample in the measuring cell 7, as well as beam-conducting means for the induction light or the light from the sample. The detection apparatus according to the invention is characterized in particular in that several essentially planar, laminar components are arranged in a sandwich structure. These components contain the sources of light 21, the measuring cell 7, the photoelectric sensing elements 22, and also the beam-conducting means.

In the following, the term "component" is understood to mean a basically planar, i.e. uncurved, and laminar structural element of the detection apparatus. It is preferable if one of the components contains all the light sources 21 arranged on one plane. Also, it is preferable if one of the components contains all the photoelectric sensing elements 22 arranged on one plane. By taking these measures, very simple adjustment is possible, as will be clarified further below.

Figure 1:
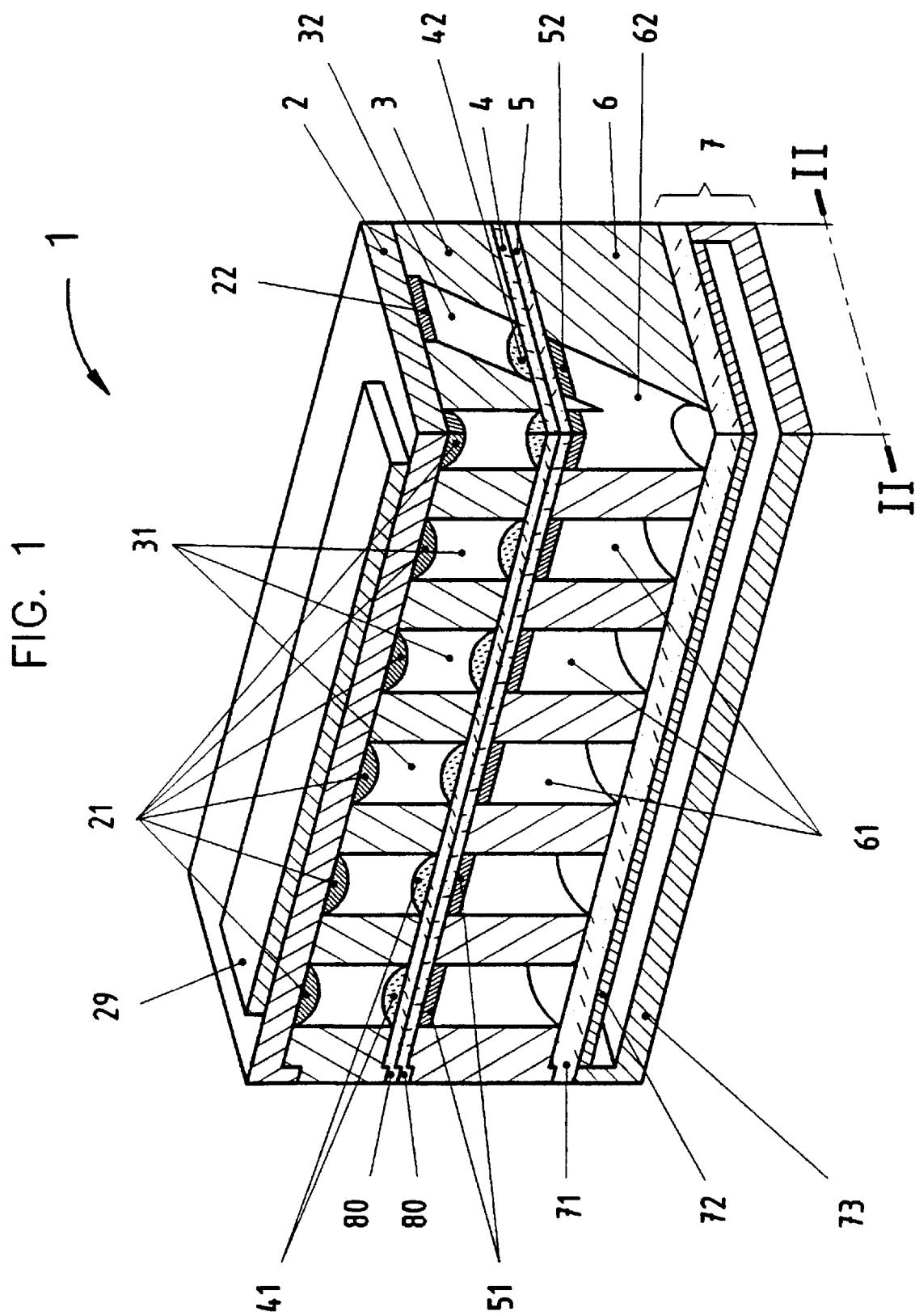
FIG. 1: a perspective double-section illustration of a first embodiment of the detection apparatus according to the invention.
Figure 2:
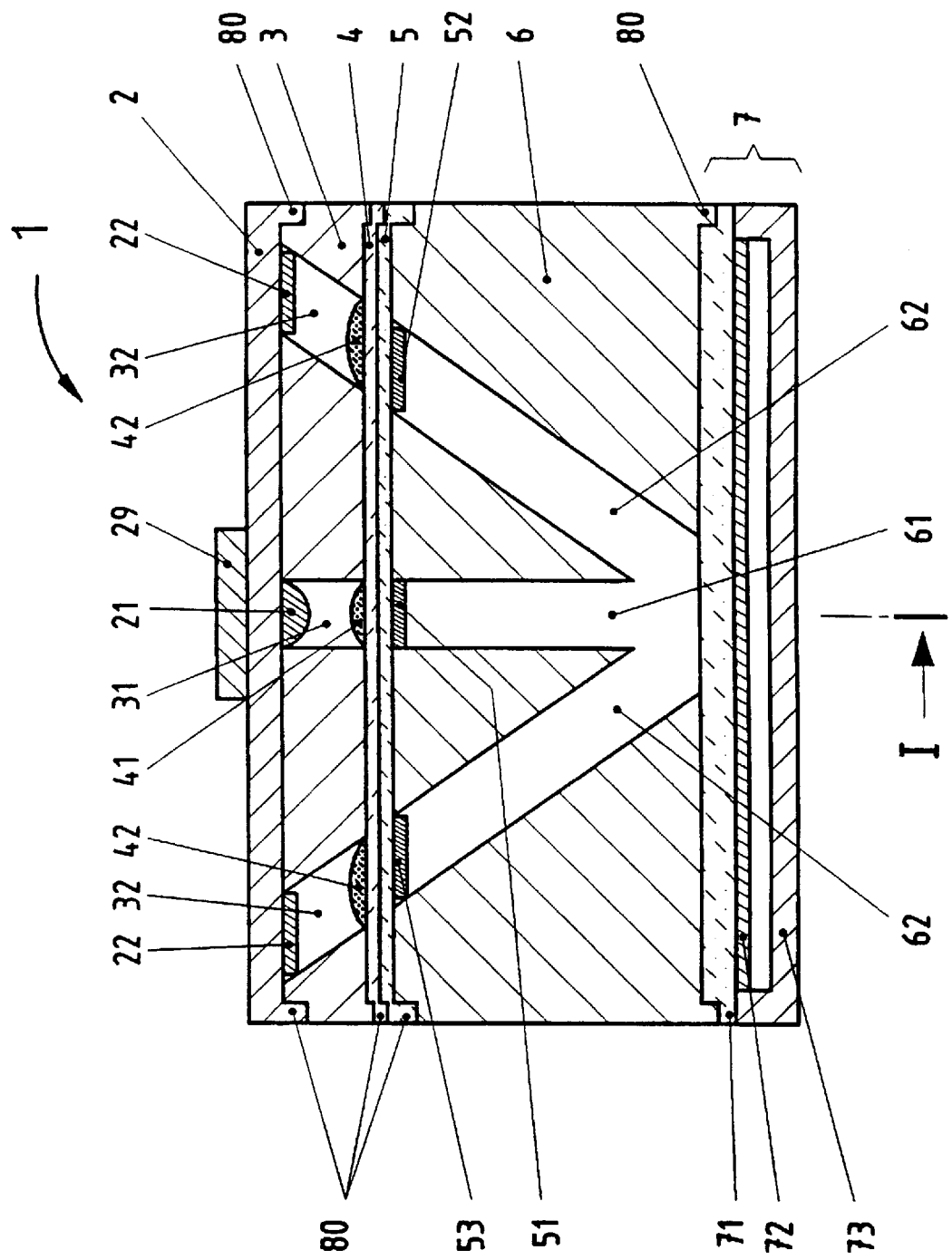
FIG. 2: a cross-section illustration of the first embodiment along the line of intersection II—II in FIG. 1, FIG. 3: a plan view of a component of the first embodiment.

FIG. 1 shows a first embodiment of the detection apparatus according to the invention in a perspective double-section illustration. It is indicated over-all by reference number 1. The two intersection lines are perpendicular to one another. FIG. 2 shows the same embodiment in a cross-section illustration. The intersection line, on which FIG. 2 is based, essentially conforms with one of the two intersection lines of FIG. 1 and is drawn in FIG. 1 as a dot-dash line II—II. The other of the two intersection lines of FIG. 1 runs vertically to the plane of the drawing in FIG. 2 and approximately in the center of the embodiment illustrated, as indicated by arrow I in FIG. 2.

The embodiment illustrated in FIG. 1 or FIG. 2 is designed for incident light measurements, i.e. the light sources 21 and the photoelectric sensing elements 22 are arranged on the same side of the measuring cell 7. This embodiment is designed in particular for fluorescence measurements.

The first embodiment comprises the following components, which are arranged in sandwich structure, in the sequence given below:

The component marked 2 contains both the light sources 21 and the photoelectric sensing elements 22. Thus, here the light sources 21 and the photoelectric sensing elements 22 are contained in the same component 2. In addition, the light sources 21 and all the photoelectric sensing elements 22 are arranged on one plane.

Attached to this component 2 is a component 3, which contains light-conducting channels 31, 32. These channels are designed like ducts.

Next attachment is a component 4, which contains optical elements 41, 42 to conduct light, for example lenses. The optical elements 41, 42 are arranged on one plane. To comprehend this more easily, this component 4 is illustrated in plan view in FIG. 3.

Following this is component 5, which contains optical filters 51 and 52, which are similarly arranged on one plane.

Component 6 follows. This in turn contains light-conducting channels 61, 62 which are designed like ducts.

Finally, there is the measuring cell 7, which in this embodiment forms a specific component. It includes a sample holder 73, a sensor layer 72 and a carrier 71, which is made e.g. of glass or plastic. The sensor layer 72 is deposited on the carrier 71, and is for example in the form of a layer of less than approximately 15 $\mu$m thickness. The carrier 71 with the sensor layer 72 basically forms an interface of the sample holder 73 in such a way that the sensor layer 72 faces the interior of the sample holder 73 and the sample can make contact with it. The sample may be at rest or also flowing in the sample holder 73. In the latter alternative, inlet and outlet apertures are of course additionally provided on the sample holder 73, but are not illustrated.

The component numbered 2 additionally includes control and evaluation equipment 29, indicated symbolically in FIGS. 1 and 2. Of course, a specific component may also be provided for the control and evaluation equipment 29.

The individual components 2–7 additionally contain connection means 80, through which they are connected to the adjacent components when in operation. These connection means 80 may be designed for example as plug connections in the form of recesses and protrusions which engage one another. In this way, components 2–7 may be simply stacked onto one another, whereby on the one hand they form a mechanically stable connection with one another, and on the other hand can be adjusted relative to one another. This self-adjustment represents a significant reduction in outlay when assembling the detection apparatus.

As FIG. 1 or 2 clearly shows, the individual components 2–7 and the parts contained therein are arranged relative to one another in such a way that they form several separate incident light measuring units, each of which comprises at least one of the sources of light 21, one of the optical filters 51, one of the optical elements 41, a light inlet channel formed by the light-conducting channels 31, 61, which conducts the induction light to the measuring cell 7, one of the photoelectric sensing elements 22, as well as a light outlet channel formed by the light-conducting channels 32, 62, which conducts the light coming from the sample in the measuring cell 7 to the photoelectric sensing element 22.

In the first embodiment, the channels 31 in component 3 are arranged so that each of the channels 31 connects one of the light sources 21 with one of the optical elements 41. The channels 32 similarly contained in component 3 are arranged so that they respectively connect one of the optical elements 42 with one of the photoelectric sensing elements 22. The channels 61 in component 6 are arranged so that they respectively connect one of the optical filters 51 with the measuring cell 7, and the channels 62 are arranged in component 6 so that they respectively connect one of the optical filters 52, 53 with the measuring cell 7. In this way, one of the channels 31 together with one of the channels 61 respectively forms a light inlet channel, while one of the channels 32 together with one of the channels 62 respectively forms a light outlet channel. Thus, in the first embodiment, the beam-conducting means comprise channels 31, 32, 61 and 62, as well as the optical elements 41 and 42.

In the cross-section illustration of FIG. 2, a complete view of one of the separate incident light measuring units of the first embodiment may be basically seen. The light source 21 emits the induction light, which goes through the light inlet channel formed by channels 31 and 61, passing the optical element 41 and the optical filter 51, and finally contacting a region of the sensor layer 72. In this embodiment, as FIG. 2 shows, in the separate incident light measuring unit there are two photoelectric sensing elements 22 and two light outlet channels, respectively formed by one of channels 62 and one of channels 32. These two light outlet channels respectively form an optical connection between one of the photoelectric sensing elements 22 and the measuring cell 7. One of the optical filters 52, 53 and one of the optical elements 42 are respectively provided in the two optical paths between the measuring cell 7 and the photoelectric sensing elements 22. Both light outlet channels are arranged at an inclination to the light inlet channel, and join the light inlet channel, so that all three light-conducting channels have a common end lying in the area of the measuring cell and forming both the light outlet area for the induction light and the light inlet area for the light from the sample.

The light inlet channels and light outlet channels additionally have the function of shields, which restrict the beam of induction light or light from the sample, and prevent optical disturbance between the individual separate incident light measuring units.

Of course, it is also possible to have variants in which there is only one light outlet channel in each of the separate incident light measuring units, and consequently also only one photoelectric sensing element 22. This light outlet channel is preferably similarly arranged at an inclination to the light inlet channel, and joins the latter, so that again both have a common end lying in the area of the measuring cell and forming both the light outlet area for the induction light and the light inlet area for the light from the sample.

As FIG. 1 and FIG. 2 show, the first embodiment comprises six separate incident light measuring units, each of which contains one of the light sources 21, one of the light inlet channels, two of the photoelectric sensing elements 22 and two of the light outlet channels. It is understood that the number of six separate incident light measuring units is by way of example. Of course, variants with more or less than six separate incident light measuring units are also possible. The method of functioning of the first embodiment will now be described using a concrete example which serves to measure fluorescence. In this example, a sample, e.g. blood, is to be examined for six analytes. The sample is placed in the sample holder 73, so that it can make contact with the sensor layer 72. The induction light produces fluorescence in the sensor layer 72, whereby the beam of fluorescence is picked up as light from the sample. If a certain analyte, which is contained in the sample and towards which the sensor layer 72 is sensitive, makes contact with the sensor layer 72, there is a change in the light from the sample, for example its intensity, which is recorded by the photoelectric sensing element 22. Sensor layers of this kind, which have selective sensitivity and change their fluorescence beam upon contact with a special analyte, are per se prior art and require no further clarification. In the first embodiment described here, the sensor layer comprises—corresponding to the number of separate incident light measuring units—six different zones, each of which is sensitive towards a different analyte.

In each of the six separate incident light measuring units (see FIG. 2), the light source 21 emits the induction light. This is transformed by the optical element 41, which is for example a lens, into an essentially parallel bundle of rays which in turn penetrates the optical filter 51. The wave length range of the induction light is limited by this optical filter 51. The induction light passed through the part of the light inlet channel formed by channel 61 and through the carrier 71 to one of the zones of the sensor layer 72, where it brings about fluorescence. The beam of fluorescence emitted from the sensor layer passes, as light from the sample, through the parts of the light outlet channels formed by channels 62 to the optical filters 52 and 53. One of the two optical filters, for example the one numbered 52, is designed such that it is essentially transparent to the light from the sample, but not to the induction light, which can similarly reach channel 62 as scattered light. The other of the two optical filters, for example the one numbered 53, is designed such that it is essentially transparent to the induction light, but not to the light from the sample. The light transmitted through the filters 52 or 53 is focused by the optical elements 42, for example lenses, onto the photoelectric sensors 22, and transformed by these into an electric signal which is available for further conversion and evaluation. Because of the different transparency of the two optical filters 52 and 53, one of the photoelectric sensing elements 22 only records the light from the sample, and the other only the induction light which is scattered in the area of the measuring cell and reaches the light outlet channels. This variant with two light outlet channels or two photoelectric sensing elements 22 has the advantage that changes in the induction light, e.g. variations in intensity, are detectable. In this way, changes in the light from the sample, which are not caused by the really interesting interaction between analyte and sensor layer, but for example by intensity fluctuations of the induction light, can be distinguished from the changes in the light from the sample which are caused by the analytes. By comparing the signals recorded by the two photoelectric sensing elements 22, one of which serves as a reference for the induction light, the accuracy of measurement may thus be controlled.

As FIG. 1 shows, the six separate incident light measuring units contact the measuring cell with the induction light in different, essentially spatially divided areas. The individual zones of the sensor layer 72 are arranged so that the separate incident light measuring units contact the sensor layer 72 with induction light in different zones. Thus, the sample may be examined for a different analyte with each of the separate incident light measuring units. Consequently, the sample may be examined in respect of several analytes at the same time. Compared with a sequential examination of the sample, this represents an enormous time saving and in addition a considerable saving in respect of the amount of sample required.

It is especially advantageous that the light sources 21, photoelectric sensing elements 22, optical elements 41, 42 and optical filters 51, 52, 53 belonging to the various separate incident light measuring units are arranged on one plane and that the channels 31, 32 and 61, 62 are respectively contained in one of the components. In this way, it is possible for all the separate incident light measuring units to be adjusted in a very simple manner in only one operation, namely by assembling the laminar components 2–7. It is therefore no longer necessary to position and adjust the distinct individual components individually in a complicated manner. This represents an enormous time saving and a considerable simplification in the assembly and handling of the detection apparatus according to the invention. Moreover, through the sandwich structure of components 2–7 and the arrangement of individual elements in the respective components, it is possible to provide an extremely compact, space-saving variant of the detection apparatus. The planar arrangement of individual elements on one plane, for example the optical elements 41, 42, which belong to different, separate incident light measuring units, brings about, apart from the simple adjustability, the additional advantage of efficient mass-production of the individual components. This situation will be explained more fully in the following, using component 4 with the optical elements 41 and 42.

Figure 3:
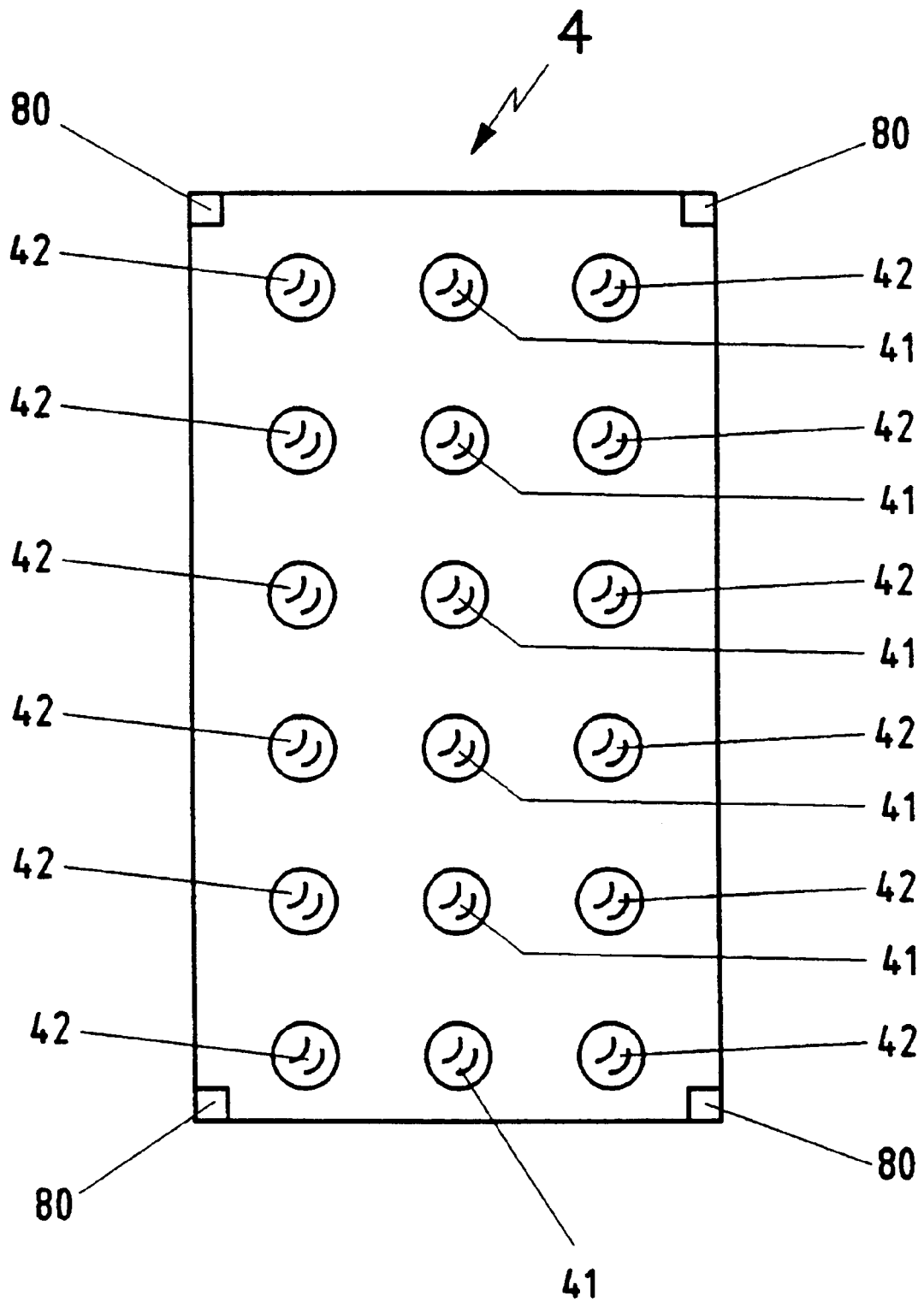

In order to comprehend it more easily, component 4 of the first embodiment is illustrated in plan view in FIG. 3. It contains a total of eighteen optical elements 41, 42, which are arranged in the form of a 6×3 matrix, whereby in each of the six rows the optical elements 42 are respectively arranged on the outside and the optical elements 41 in the center. Each of the six rows belongs to a different, separate incident light measuring unit. As already mentioned, in the first embodiment, the optical elements 41, 42 are for example lenses, whereby the optical elements 41 arranged in the central column serve to transform the induction light into a parallel bundle of rays, while the optical elements 42 arranged in the two outer columns focus the light coming from the measuring cell 7 onto the photoelectric sensing elements 22. Thus, all the optical elements 41, 42 of the first embodiment, which act as beam conductors, are arranged on one plane in the form of a field. In an especially preferred variant, the optical elements 41, 42 are micro-optical elements, for example micro-lenses. By micro-lenses are understood those lenses which have a diameter of at most 2 mm. Such a field of micro-lenses offers the advantage that they may be produced very inexpensively in large quantities, with very good reproducibility, by means of efficient mass-production. Production is carried out for example by means of known replication techniques. To do so, first of all a master is produced according to the desired arrangement of the micro-optical elements. This is a single piece, which serves as a basis for replication. Such masters are produced by technology which is usual in micro-optics or semi-conductor manufacture, for example resistance technology, lithography, masking technology, coating, etching, diamond turning, polishing technology. From this master, stamp dies or the like are produced, with which the micro-optical elements or the fields of micro-optical elements are manu-factured by known replication technology, e.g. CD technology, stamping processes, casting processes, pressure technology. The material used for the micro-optical elements may be for example polymethyl methacrylate (PMMA), polycarbonate or epoxy resin. Compared with other distinct beam-conducting optical elements, for example GRIN lenses or optical fibres, a field of micro-lenses is consider-ably less expensive to produce. In addition, there is a considerable time saving, since through the planar arrange-ment of the micro-lenses in one field, all the lenses may be adjusted in one operation and each individual optical ele-ment does not have to be individually positioned and adjusted.

In addition, the use of micro-optical elements is also very advantageous in respect of miniaturization. With consider-ably smaller dimensions, micro-optical elements can carry out basically the same optical functions as for example GRIN lenses or similar optical elements, and thus enable the detection apparatus to be further miniaturized. For example, micro-lenses can be produced using conventional modern technology with diameters of a few μm. Of course, in the detection apparatus according to the invention, other micro-optical elements may be employed, apart from micro-lenses. These micro-optical elements may take on different optical functions depending on the application, a few of which are mentioned in the following, but do not constitute a complete list: collimation, focusing, deflection of the whole bundle of rays, division of the bundle of rays, forming a bundle of rays, light diffusion, imaging.

The micro-optical elements may be designed as refractive, diffractive or hybrid micro-optical elements. The optical functions of the refractive elements are essentially determined by their surfaces. These refractive elements are designed using the laws of geometrical optics, i.e. their properties are determined by refraction, diffraction or reflec-tion of light rays on optical transitions (transitions between areas of optically different density), and are essentially independent of wave length. Diffractive optical elements are normally planar and include zones which influence the incident light waves e.g. by modulation of the refractive index. The light coming from the differing zones interferes and thus forms the desired light wave front. The optical properties of the diffractive elements are strongly dependent on wave length. In order to make use of the advantages of the refractive elements—namely the minimal dispersion—and the advantages of the diffractive elements—namely the multiple functions—, it is advantageous to use hybrid micro-optical elements which are mixed forms between refractive and diffractive elements.

Furthermore, it is possible to use the micro-optical ele-ments as connecting means for component 4. To this end, further micro-optical elements, which are not illustrated in FIG. 3, may be provided for example in the peripheral area of component 4. These do not take on an optical function during operation, but serve to adjust component 4 in relation to its adjacent components.

It is also possible to color the micro-optical elements, so that they take on the function of optical filters at the same time.

In analogous manner to that described above, it is also possible to design the optical filters 51, 52, 53 in component 5 as micro-optical filters.

Figure 4:
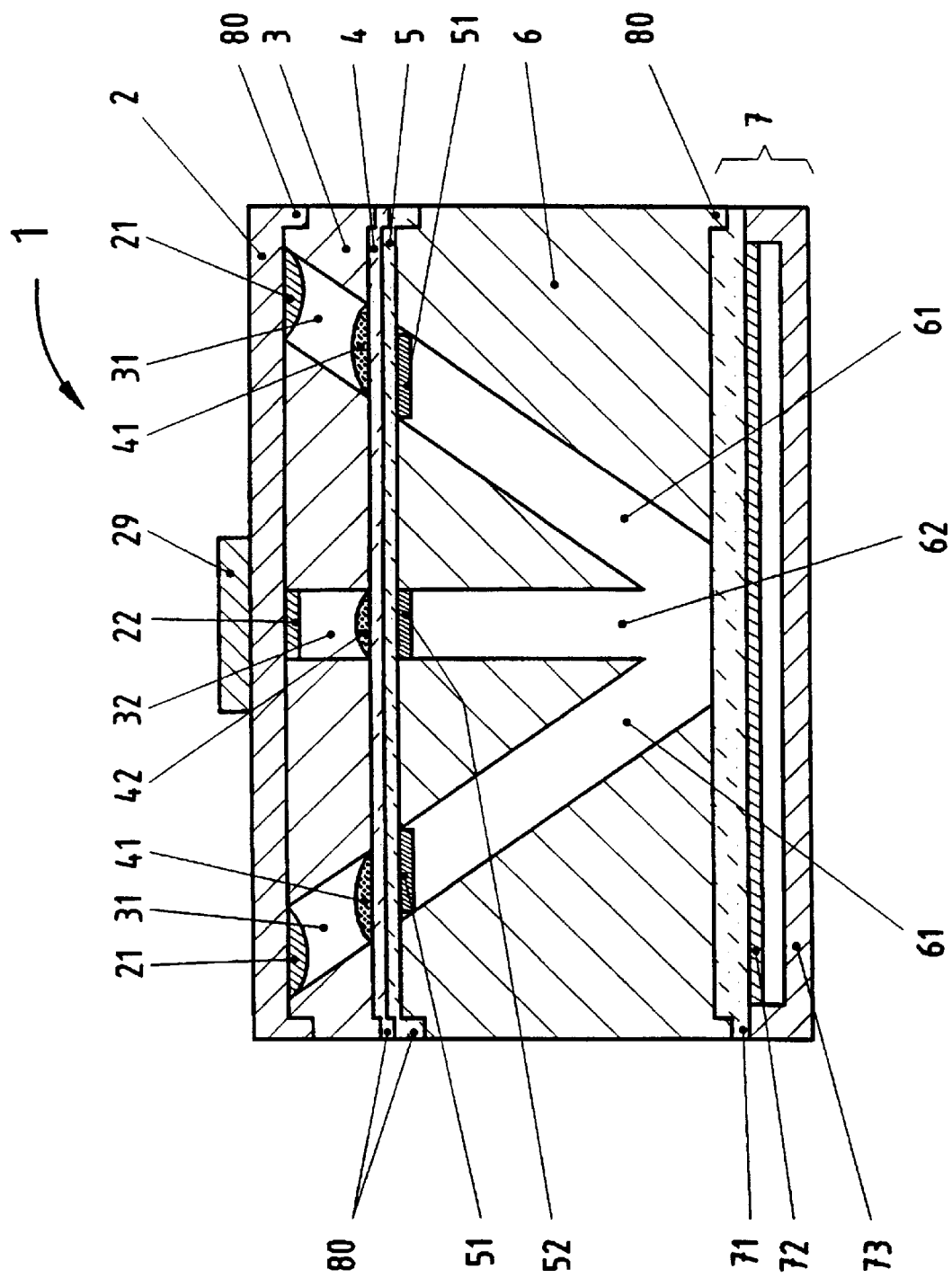
FIG. 4: a cross-section illustration analogous to FIG. 2 for a variant of the first embodiment.

FIG. 4 illustrates a variant of the first embodiment of the optical detection apparatus according to the invention in cross-section—analogously to FIG. 2. The mechanical con-struction is essentially the same as that illustrated in FIG. 2. The essential difference is that in the variant illustrated in FIG. 4, in each of the separate incident light measuring units, there are two light sources 21 and only one photoelectric sensing element 22. The arrangement of channels 31, 32, 61, 62 is essentially the same as that shown in FIG. 2. Only their function has changed. The two light outlet channels (FIG. 2) now serve (FIG. 4) as light inlet channels, and the light inlet channel (FIG. 2) in this variant (FIG. 4) serves as a light outlet channel.

Thus, in this variant, as shown in FIG. 4, in each separate incident light measuring unit there are two light sources 21 and two light inlet channels, which are respectively formed by one of channels 31 and one of channels 61. These two light inlet channels respectively form an optical connection between one of the light sources 21 and the measuring cell 7. In the two optical paths between the light sources 21 and the measuring cell 7, there is respectively one of the optical filters 51 which restricts the area of wave length range of the induction light and one of the optical elements 41. The light coming from the sample in the measuring cell 7 is emitted through the light outlet channel formed by channels 62 and 32, passes the optical filter 52 which restricts the wave length range of the light from the sample and passes the optical element 42, and finally contacts the photoelectric sensing element 22.

The two light inlet channels are arranged at an inclination to the light outlet channel and join the light outlet channel, so that all three light-conducting channels have a common end lying in the area of the measuring cell and forming both the light outlet area for the induction light and the light inlet area for the light from the sample.

Consequently, in each of the separate incident light mea-suring units, two light sources 21 are available, which, because of the arrangement of the light inlet channels, essentially contact the same area of the measuring cell 7 with induction light. In this way, the two light sources 21 belong-ing to the same separate incident light measuring unit can emit induction light of the same wave length or of different wave lengths. The first alternative offers the advantage that the entire light intensity, with which one of the separate incident light measuring units contacts the measuring cell, increases, and the second alternative offers the possibility of contacting the sensor layer 72 with differing wave lengths or wave length ranges, with the result that there is a reduction in disturbances caused for example by scattered light, and thus an increase in accuracy of measurement. The two light sources 21 can contact the measuring cell 7 with the induction light either simultaneously or at different times.

Figure 5:
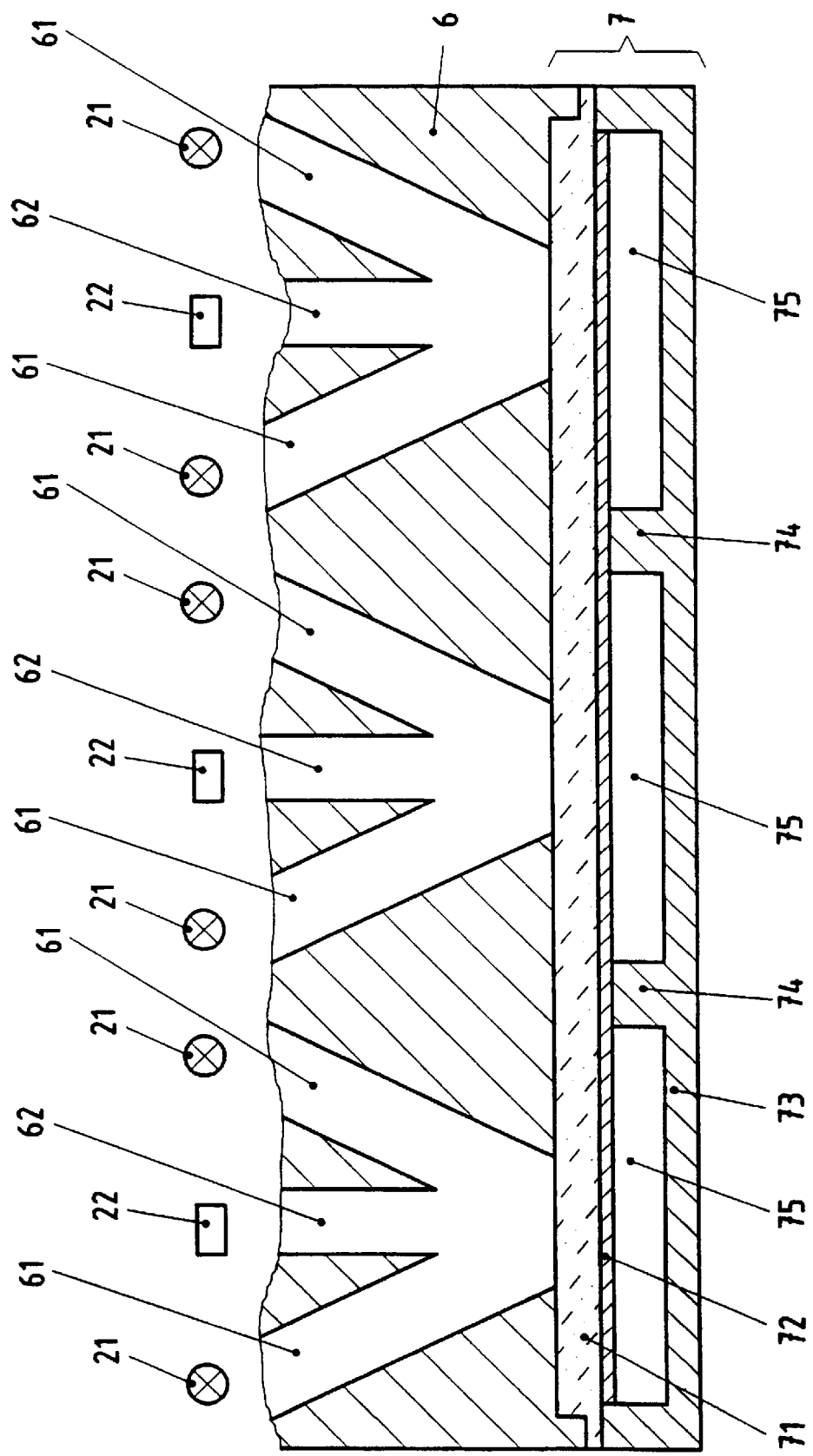
FIG. 5: a section of a further variant of the first embodiment in cross-section.
Figure 6:
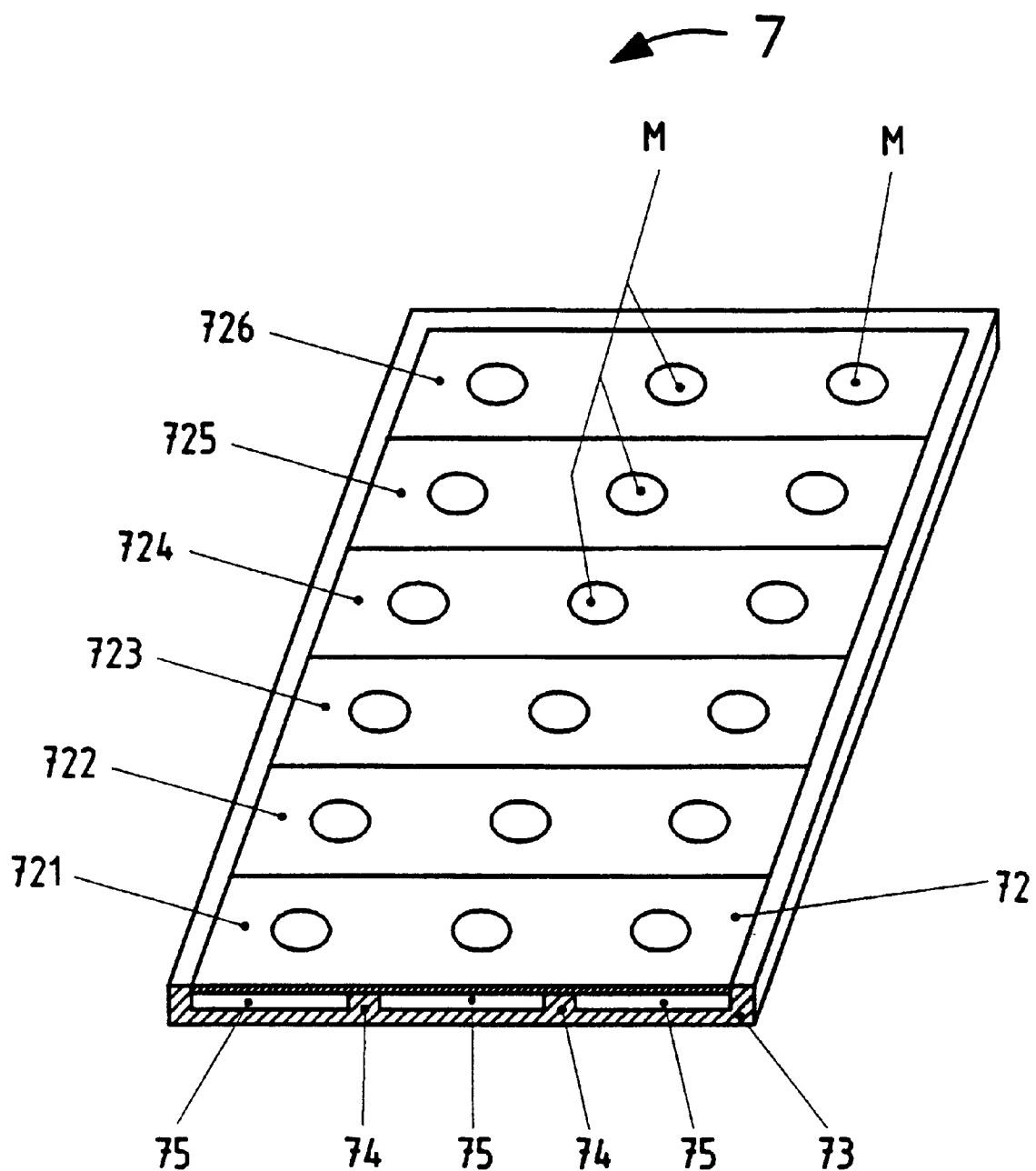
FIG. 6: a perspective illustration of a measuring chamber of the variant from FIG. 5 (without carrier, front view in section)

FIG. 5 shows another section of a further variant of the first embodiment of the optical detection apparatus according to the invention, in cross-section. For a better overview, and since this is sufficient to understand the drawing, only components 6 and 7 are illustrated in FIG. 5. In this variant, there are a total of eighteen separate incident light measuring units, which are arranged in six rows with three in each, thus forming a field (array). The explanations given above respectively apply to each of these separate incident light measuring units. It is understood that the optical filters 51, 52, 53, and the optical elements 41, 42 are provided in each. Thus, in this variant, component 4 comprises all together fifty-four optical elements, which are all arranged on one plane. Similarly, component 5 comprises a total of fifty-four optical filters 51, 52, 53. The light sources 21 and the photoelectric sensing elements 22 are only indicated symbolically in FIG. 5. The sample holder 73 is divided by partitions 74 into three separate sample chambers 75. For better comprehension, FIG. 6 shows a perspective view of the measuring chamber 7 of the variant shown in FIG. 5, but without the carrier 71, whereby the front is shown in section. The circles indicated by the letter M are symbolic representations of the spatially divided areas of the measuring cell 7, which are contacted by induction light from the eighteen separate incident light measuring units. Each of the circles M thus indicates the position of one of the light outlet or light inlet areas of the separate incident light measuring units. It can clearly be seen that the regions contacted by the induction light are arranged two-dimensionally in the form of a 6×3 matrix. In this variant, the sensor layer 72 comprises six different zones 721–726, which are sensitive towards different analytes. As FIG. 6 shows, in each of these six zones 721–726, there are three contact areas next to one another, so that for each of zones 721–726, there are three essentially separate measuring units available.

This variant with the eighteen separate incident light measuring units offers the advantage that calibration measurements can be carried out at the same time as the actual analysis, which brings about an improvement in the accuracy of analysis and makes any prior calibration of the detection apparatus unnecessary. To this end, two liquids are used, each of which contains the analytes to be detected—in this precise example six—in known concentration. One of the liquids may contain the analytes, for example in a concentration corresponding to the minimum of the range of measurement in question, and the other liquid may contain the analytes in a concentration corresponding to the maximum of the range of measurement in question. One of the liquids is placed for example in one of the two outside sample chambers, and the other liquid in the other outside sample chamber. The sample to be analysed, which contains the analytes in unknown concentration, will be placed in the center sample chamber. From the fluorescence measurement, or from the change in fluorescence, there will be three measured values for each of zones 721–726, two of which stem from known concentrations of the respective analyte and one from the unknown concentration in the sample. In this way, with each measurement, calibration is effected in each of zones 721–726, with the result that a considerably greater accuracy of analysis is attained. In addition, owing to the calibration which is synchronous with the analysis, degradation effects in the sensor layer can be detected very simply.

Of course, the variant shown in FIG. 5 may also be designed such that the separate incident light measuring units are formed as in the embodiment illustrated in FIG. 2.

It is understood that in the variant shown in FIGS. 5 and 6, the number of eighteen separate incident light measuring units, and their arrangement in six rows of three, is illustrated by way of example. Depending on the application, other arrangements or other numbers are also possible.

FIG. 7 illustrates a second embodiment of the optical detection apparatus according to the invention in cross-section. It is designed for measuring transmitted light, i.e. the component with the measuring cell 7 is arranged between the component with the light sources 21 and the component with the photoelectric sensing elements 22. This second embodiment is suitable for example for absorption measurements.

The second embodiment comprises components 2a, 3a, 4a, 6a, 7, 6b, 4b, 3b, 2b, which are arranged in sandwich structure, in the sequence given as follows:

The component numbered 2a contains the light sources 21 which are arranged on one plane. Following this is a component 3a, which contains light-conducting channels 31a. These channels are designed as ducts. Next is component 4a, which contains the optical elements 41 to conduct the induction light, for example lenses. The optical elements 41 are arranged on one plane. The next component 6a contains light-conducting channels 61a, which are again designed as ducts. Component 7 follows, and in this embodiment forms the measuring cell 7. It includes a cover plate 71a and the sample holder 73, whereby the cover plate 71a covers the sample holder 73 so that the two form an essentially sealed sample chamber 75a for the sample. The sample may be at rest or also flowing in the sample chamber 75a. In the latter alternative, inlet and outlet apertures are of course additionally provided on the sample holder 73, but are not illustrated. On the other side of the measuring cell 7 there is component 6b, which includes light-conducting channels 62b that are designed as ducts. Component 4b follows, and contains the optical elements 42 to conduct light from the sample. The optical elements 42, for example lenses, are arranged on one plane in component 4b. Component 3b follows component 4b, and contains channels 32b to conduct light from the sample. The channels 32b are designed as ducts. Finally, component 2b is next. This contains the photoelectric sensing elements 22, arranged on one plane.

In this embodiment also, of course, control and evaluation equipment may be provided, which are arranged for example in component 2a or 2b or in a specific component, but are not illustrated.

The individual components 2a,3a,4a,6a,7,6b,4b,3b,2b—analogously to the first embodiment—additionally contain connection means 80, through which they are connected to the adjacent components when in operation. These connection means 80 enable the individual components on the one hand to be stably connected to one another and on the other hand to be adjusted relative to one another.

As FIG. 7 shows, the individual components 2a,3a,4a, 6a,7,6b,4b,3b,2b and the parts contained in them are arranged relative to one another, so that they form several separate transmitted light measuring units, each of which comprises one of the light sources 21, one of the optical elements 41, a light inlet channel formed by channels 31a, 61a to conduct the induction light to the measuring cell 7, one of the photoelectric sensing elements 22, as well as a light outlet channel formed by channels 32b, 62b, to conduct the light coming from the sample in the measuring cell 7 to the photoelectric sensing element 22.

In the second embodiment, the channels 31a in component 3a are arranged so that each of the channels 31a connects one of the light sources 21 with one of the optical elements 41. The channels 61a in component 6a are arranged so that they respectively connect one of the optical elements 41 with the measuring cell 7, and the channels 62b are arranged in component 6b so that they respectively connect one of the optical elements 42 with the measuring cell 7. The arrangement of channels 32b in component 3b is such that each of the channels 32b connects one of the optical elements 42b with one of the photoelectric sensing elements 22. In this way, one of the channels 31a together with one of the channels 61a forms a light inlet channel, while one of the channels 32b together with one of the channels 62b forms a light outlet channel. In the second embodiment, the beam-conducting means thus comprises channels 31a, 32b, 61a and 62b, as well as the optical elements 41 and 42.

In the second embodiment illustrated in FIG. 7, there are five separate transmitted light measuring units. In each of these, the light source 21 emits the induction light, which travels through the light inlet channel formed by channels 31a and 61a, passes the optical element 41 and finally makes contact with an area of the measuring cell 7. The light coming from the sample in the measuring cell is conducted through the light outlet channel, passes the optical element 42 and contacts the photoelectric sensing element 22, which converts it into an electric signal which is available for further processing and evaluation.

The light inlet and outlet channels additionally take over the function of screens, which restrict the beam of the induction light or of the light from the sample and prevent disturbances between the individual separate transmitted light measuring units. The optical elements 41 are for example lenses, which respectively transform the induction light coming from the light sources into a parallel light bundle. The light inlet channels are preferably arranged such that the induction light coming from them makes essentially vertical contact with the measuring cell 7, so that disturbances between the individual separate transmitted light measuring units is suppressed. The optical elements 42 in the light path of the sample are for example lenses, which respectively focus the light from the sample onto one of the photoelectric sensing element 22.

The separate transmitted light measuring units most preferably contact the measuring cell 7 at different, essentially spatially separated areas, as shown by FIG. 7. The individual light sources 21 can then for example emit induction light of different wave lengths or wave length ranges. This makes it possible to carry out absorption measurements in different wave length ranges simultaneously in one measuring operation.

It is understood that the number of separate transmitted light measuring units in the second embodiment is by way of example. Of course, other variants with more or less than five separate transmitted light measuring units are possible. The separate transmitted light measuring units may also be two-dimensional, that is, arranged in the form of a field, in analogous manner to that described above for the first embodiment (see e.g. FIG. 6).

Of course, in the second embodiment there may also be components with optical filters. It is also possible for each of the separate transmitted light measuring units to comprise more than one photoelectric sensing element 22, for example to produce a reference signal, as described above.

It is understood that the above-mentioned explanations relating to the first embodiment or its variants also apply in an appropriate manner to the second embodiment. In particular, in the second embodiment, the optical elements 41, 42 are also most preferably micro-optical elements, for example micro-lenses, which are respectively arranged on one plane.

It is also possible to have variants of the optical detection apparatus according to the invention, which comprise both separate incident light measuring units and separate transmitted light measuring units. Furthermore, the separate measuring units may be formed such that they enable transmitted light and incident light measurements to be made in one measuring unit.

Of course, further components may also be contained in the apparatus, for example an additional component with optical elements.

It is preferable for the light sources 21 in the optical detection apparatus according to the invention to be light-emitting diodes (LED). These are preferred, since, being equipped with stabilized power sources, they are far more stable in respect of light intensity than lasers or other conventional light sources. They have practically no intensity fluctuation, which is advantageous for accuracy of measurement.

The optical detection apparatus according to the invention for chemical analysis of small volumes of samples is notable in particular for its sandwich structure with several, essentially planar, laminar components. Because of this structure, the apparatus may be very simply assembled, adjusted and handled. The individual, essentially separate measuring units enable simultaneous analysis of several analytes to take place. The respectively planar arrangement of individual components, such as optical elements, light sources, optical filters or photoelectric sensing elements, on one plane is especially advantageous. In this manner, the individual separate measuring units may be adjusted simultaneously in only one operation. Complicated positioning and adjustment of the individual distinct components is no longer necessary.

The use of micro-optical elements or fields with such elements is particularly advantageous. The reason is that these may be produced very inexpensively, with good reproducibility, by means of established, efficient mass-production processes. In addition, the use of micro-optical elements allows the apparatus to be miniaturized, which is not achievable with other optical elements. In this way, there is a saving both in the time taken for analysis and in the amount of sample employed. Sample volumes in the region of a few micro-liters may be reliably examined in respect of several analytes.

Through the planar arrangement of the individual elements, which belong to the different separate measuring units, in the respective components, the apparatus maintains an extremely compact and robust form, which enables it to be used even outside of modern research laboratories. In addition, the sandwich concept in which the individual components are simply stacked together in the manner of a module system brings with it the advantage of very great flexibility, so that the apparatus according to the invention may be used for very many fields of application, for example in medicine, in agriculture, in environmental technology or for monitoring processes. In particular, the optical detection apparatus according to the invention is also suitable for immuno-assay.

What is claimed is:

1. Optical detection apparatus for chemical analyses of small volumes of samples, comprising:

a measuring cell for receiving the sample;

light sources for emitting induction light to the measuring cell;

photoelectric sensing elements for receiving light from the sample in said measuring cell; and light conducting channels for conducting the induction light to the sample in said measuring cell and for conducting the light from the sample in said measuring cell to said photoelectric sensing elements;

wherein a plurality of essentially planar, laminar components are arranged in a sandwich structure, said components containing said measuring cell, said light sources, said photoelectric sensing elements and said light conducting channels.

2. The apparatus of claim 1, wherein said components comprise respective connections connecting said components to adjacent said components in said sandwich structure.

3. The apparatus of claim 1, wherein one of said components comprises a plurality of light conducting optical elements arranged on one plane.

4. The apparatus of claim 3, wherein one of said components comprises said light sources arranged on one plane.

5. The apparatus of claim 4, wherein one of said components comprises said photoelectric sensing elements arranged on one plane.

6. The apparatus of claim 1, wherein said light conducting channels comprise ducts.

7. The apparatus of claim 1, wherein said measuring cell is provided in one of said components that is disposed between two other of said components provided with said light sources and said photoelectric sensing elements.

8. The apparatus of claim 1, wherein:

said measuring cell, said light sources, said photoelectric sensing elements, said light conducting channels and optical elements are arranged relative to each other so as to form a plurality of separate transmitted light measuring units;

said light conducting channels comprise light inlet channels and light outlet channels;

each of said units comprises one of said light sources, one of said optical elements, one of said light conducting channels for conducting induction light to measuring cell, one of said photoelectric sensing elements and one of said light outlet channels for conducting light from the sample in said measuring cell to the one of said photoelectric sensing elements.

9. The apparatus of claim 8, wherein each of said units further comprises an additional one of said optical elements arranged between said measuring cell and said photoelectric sensing element.

10. The apparatus of claim 8, wherein each of said light inlet channels is arranged so that induction light that is emitted therefrom contacts said measuring cell essentially perpendicularly thereto.

11. The apparatus of claim 8, wherein said units are arranged so that induction light from respective said units contacts said measuring cell at different spatially divided areas of said measuring cell.

12. The apparatus of claim 1, wherein one of said components contains both said light sources and said photoelectric sensing elements arranged on one plane.

13. The apparatus of claim 12, wherein said components comprise a component which contains optical filters arranged on one plane.

14. The apparatus of claim 13, wherein said optical filters comprise micro-optical filters.

15. The apparatus of claim 13, wherein:

said measuring cell, said light sources, said photoelectric sensing elements, said light conducting channels and said optical elements are arranged relative to each other so as to form a plurality of separate transmitted light measuring units;

said light conducting channels comprise light inlet channels and light outlet channels; and each of said units comprises one of said light sources, one of said optical elements, one of said light conducting channels for conducting induction light to measuring cell, one of said photoelectric sensing elements and one of said light outlet channels for conducting light from the sample in said measuring cell to the one of said photoelectric sensing elements.

16. The apparatus of claim 15, wherein in each of said units, said light inlet channel and said light outlet channel are inclined with respect to each other and intersect so as to have a common end that lying in an area of said measuring cell that forms both a light outlet area for induction light and a light inlet area for light from the sample.

17. The apparatus of claim 16, wherein each of said units further comprises a further photoelectric sensing element optically linked by a respective further light outlet channel to said measuring cell, said further light outlet channel being inclined with respect to said light inlet channel and intersecting with light inlet channel.

18. The apparatus of claim 16, wherein each of said units further comprises a further light source optically linked by a respective further light inlet channel to said measuring cell, said further light inlet channel being inclined with respect to said light outlet channel and intersects said light outlet channel.

19. The apparatus of claim 15, wherein in each of said units, one of said optical elements is provided between each of said light sources and said measuring cell, and a further one of said optical elements is provided between each of said photoelectric sensors and said measuring cell, said one and said further one of said optical elements being arranged on one plane.

20. The apparatus of claim 15, wherein in each of said units, one optical filter is provided between each of said light sources and said measuring cell, and a further optical filter is provided between each of said photoelectric sensors and said measuring cell, said one and said further said optical filters being arranged on one plane.

21. The apparatus of claim 15, wherein said units are arranged so that induction light from respective said units contacts said measuring cell at different spatially divided areas of said measuring cell.

22. The apparatus of claim 21, wherein said units are arranged so that said areas of said measuring cell are arranged two-dimensionally.

23. The apparatus of claim 22, wherein said measuring cell comprises a sensor layer that can be contacted by the sample and by induction light.

24. The apparatus of claim 23, wherein said sensor layer comprises different zones which are sensitive to respective different analytes.

25. The apparatus of claim 24, wherein said optical elements comprise micro-optical elements.

26. The apparatus of claim 25, wherein said micro-optical elements are refractive or diffractive or hybrid micro-optical elements.

27. The apparatus of claim 1, wherein said measuring cell comprises a plurality of sample chambers.

28. The apparatus of claim 1, where+in said light sources comprise light-emitting diodes.

29. The apparatus of claim 1, wherein one of said components comprises control and evaluation equipment.

* * * * *